US00RE43688E

(19) United States
(12) Reissued Patent
Mukherjee et al.

(10) Patent Number: US RE43,688 E
(45) Date of Reissued Patent: Sep. 25, 2012

(54) COMPOSITIONS AND METHODS RELATED TO SEROTONIN 5-HT1A RECEPTORS

(75) Inventors: Jogeshwar Mukherjee, Irvine, CA (US); Neil Saigal, Fresno, CA (US); Harsh Saigal, legal representative, Fresno, CA (US)

(73) Assignee: The Regents of the University of California, Oakland, CA (US)

(21) Appl. No.: 13/187,728

(22) Filed: Jul. 21, 2011

Related U.S. Patent Documents

Reissue of:
(64) Patent No.: 7,731,940
Issued: Jun. 8, 2010
Appl. No.: 11/626,797
Filed: Jan. 24, 2007

U.S. Applications:
(60) Provisional application No. 60/762,444, filed on Jan. 25, 2006.

(51) Int. Cl.

| | |
|---|---|
| ***A61K 31/55*** | (2006.01) |
| ***C07D 401/00*** | (2006.01) |
| ***A61K 49/04*** | (2006.01) |
| ***A61K 31/497*** | (2006.01) |
| ***C07D 241/04*** | (2006.01) |

(52) U.S. Cl. .... 424/9.4; 544/360; 544/358; 514/252.12; 514/213.01

(58) Field of Classification Search ..... None
See application file for complete search history.

(56) References Cited

U.S. PATENT DOCUMENTS

| | | | |
|---|---|---|---|
| 5,135,931 | A | 8/1992 | Carlier et al. |
| 5,609,849 | A | 3/1997 | Kung |
| 5,744,121 | A | 4/1998 | Kung |
| 5,789,412 | A | 8/1998 | Halazy et al. |
| 6,056,942 | A | 5/2000 | Cliffe et al. |
| 6,103,725 | A | 8/2000 | Kennis et al. |
| 6,224,849 | B1 | 5/2001 | Kennis et al. |
| 6,670,400 | B1 | 12/2003 | Bigg et al. |
| 6,821,981 | B2 | 11/2004 | Stack et al. |
| 6,831,084 | B1 | 12/2004 | Childers, Jr. et al. |
| 6,861,427 | B2 | 3/2005 | Stack et al. |

FOREIGN PATENT DOCUMENTS

| | | |
|---|---|---|
| EP | 0512755 | 4/1992 |
| WO | 93/11122 | 6/1993 |
| WO | 93/14076 | 7/1993 |
| WO | 94/19026 | 9/1994 |
| WO | 96/01656 | 1/1996 |
| WO | 2005/121796 | 12/2005 |

OTHER PUBLICATIONS

Mueller. Alzheimer's & Dementia, 2005, 1, 55-66.*
Turner. Age and Ageing, 2004, 33, 461-467.*
McGuire. Trends in Pharmacological Sciences, 2008, 29(2), 91-98.*
Osman. Nuclear Medicine and Biology, 1998, 25, 215-223.*
Nemeroff. Journal of Psychiatric Research, 2007, 41, 189-206.*
Wilson. Nuclear Medicine and Biology, 1996, 23, 487-490.*
Wilson. Nuclear Medicine and Biology, 1998, 25, 769-776.*
Pike. European Journal of Pharmacology, 1995, 283, R1-R3.*
Saigal, et al., Synthesis and Biologic Evaluation of a Novel Serotonin 5-HT Receptor Radioligand, F-Labeled Mefway, in Rodents and Imaging by PET in a Nonhuman Primate, Journal of Nuclear Medicine, Oct. 2006, pp. 1697-1706, vol. 47 No. 10, Society of Nuclear Medicine.
Kepe, et al., Serotonin 1A Receptors in the Living Brain of Alzheimer's Disease Patients, Proceedings of the National Academy of Science of the US, Jan. 9, 2006, pp. 702-707, issue 103, PNAS 2006, online.
Brust, et al., In vivo Measurements of the Serotonin Transporter with (S)-([18F]fluoromethyl)-(+)-McN5652, Neuropsychopharmacology, 2003, pp. 2010-2019, vol. 28, Nature Publishing Group, online.
Cliffe, A Retrospect on the Discovery of WAY-100635 and the Prospect for Improved 5-HT1a Receptor PET Radioligands, Nuclear Medicine & Biology, Apr. 2000, pp. 441-447, vol. 27, Elsevier Science Inc.
Lang, L et al., "Development of Fluorin-18-Labeled 5-HT1a Antagonists", Journal of Medical Chemistry, 1999, vol. 42, pp. 1576-1586.
Bailey, D.L. et al, "Positron Emission Tomography: Basic Sciences", Springer, Mar. 2005, Chapter 6—Tracer Kinetic Modeling in PET* (pp. 127-159), and Chapter 9—Radiohalogens for PET Imaging* (pp. 203-222).
Green, A.R. et al, "Therapeutic strategies for the treatment of stroke", Drug Discovery Today, Aug. 2006, vol. 11, No. 15/16, pp. 681-693.
Griogiadis, D.E. et al, "The corticotropin-releasing factor receptor: a novel target for the treatment of depression and anxiety-related disorders", Expert Opinion, Therapeutic Targets, 2005, vol. 9, No. 4, pp. 651-684.
Langstrom, B, et al, "Compounds Labelled with Short-Lived B+-Emitting Radionuclides and Some Applications in Life Science. The Importance of Time as a Parameter", Act Chemica Scandinavica, 1999, vol. 53, pp. 651-669.
"Movement Disorders", National Library of Medicine—Medical Subject Headings, 2009.
Neurodegenerative Diseases, National Library of Medicine—Medical Subject Headings, 2008.
Wong, A.H.C., et al, "Potential therapeutic targets for schizophrenia", Emerging Therapeutic Targets: Central & Peripheral Nervous Systems, 1999, vol. 3, No. 4, pp. 571-586.
Wong et al. Emerging Therapeutic Targets, 1999, 3(4), 571-586.*
Grigoriadis .xpert Opinion on Therapeutic Targets, 2003, 9 (4), 651-84.*
Green et al. Drug Discovery Today, 2006, 11 (15/16), 681-693.*
Langstrom et al. Acta Chimica Scandinavica, 1999, 53, 651-69.*
Bailey et al (editors of Positron Emission Tomography, published 2005, chapter 6, pp. 127-159, and chapter 9, pp. 203-222.*
"Neurodegenerative diseases", http://www.nlm.nih.gov/cgi/mesh/2008/MB_cgi, accessed Dec. 8, 2008, attached as PDF.*
"Movement Disorders", http://www.nlm.nih.gov/cgi/mesh/2009/MB_cgi?mode=&index=8693&field=all&HM=&II=&PA=&form=&input=, accessed Jul. 13, 2009, attached as PDF.*
Lang et al. Journal of Medicinal Chemistry, 1999, 42, 1576-86.*

* cited by examiner

*Primary Examiner* — Noble Jarrell
(74) *Attorney, Agent, or Firm* — Fish & Associates, PC

(57) ABSTRACT

Contemplated substituted arylpiperazinyl compounds, and most preferably $^{18}$F-Mefway, exhibit desirable in vitro and in vivo binding characteristics to the 5-HT1A receptor. Among other advantageous parameters, contemplated compounds retain high binding affinity, display optimal lipophilicity, and are radiolabeled efficiently with $^{18}$F-fluorine in a single step. Still further, contemplated compounds exhibit high target to non-target ratios in receptor-rich regions both in vitro and in vivo, and selected compounds can be effectively and sensitively displaced by serotonin, thus providing a quantitative tool for measuring 5-HT1A receptors and serotonin concentration changes in the living brain.

18 Claims, 5 Drawing Sheets

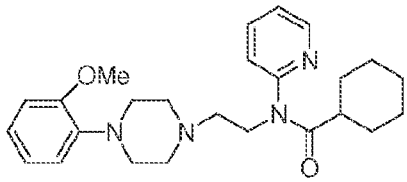
WAY-100635
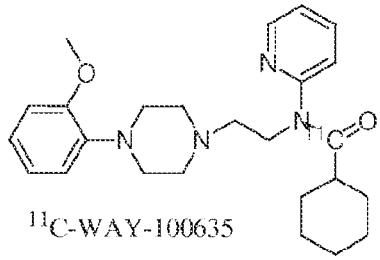
$^{11}$C-WAY-100635
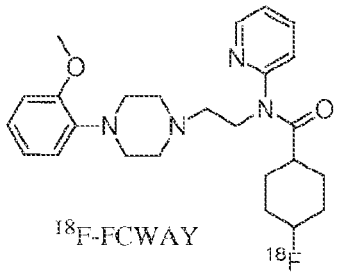
$^{18}$F-FCWAY
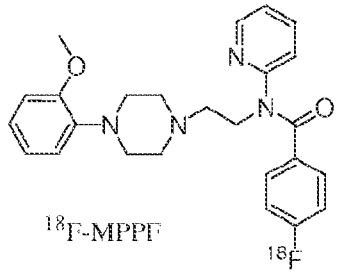
$^{18}$F-MPPF
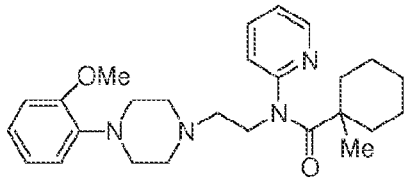
SWAY
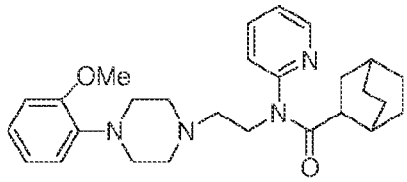
CPC-222
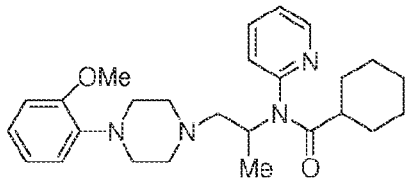
(*R,S*)-JWAY
Prior Art Figure 1

COMPOSITIONS AND METHODS RELATED TO SEROTONIN 5-HT1A RECEPTORS

Matter enclosed in heavy brackets [ ] appears in the original patent but forms no part of this reissue specification; matter printed in italics indicates the additions made by reissue.

This application claims the benefit of our U.S. provisional patent application with the Ser. No. 60/762,444, which was filed Jan. 25, 2006, and which is incorporated by reference herein.

This invention was made with government support from the NIH Grant No. R21AG030524-01 from the National Institute on Aging and Biological and Environmental Research Program (BER), U.S. Department of Energy, using Grant No. DE-FG03-02ER63294. The government may have certain rights in the invention.

FIELD OF THE INVENTION

The field of the invention is compositions and methods of synthetic receptor ligands, and especially as they relate to radiolabeled ligands for PET and/or SPECT analysis.

BACKGROUND OF THE INVENTION

Serotonin 5-HT1A receptors are implicated in Alzheimers disease, dementia, anxiety, schizophrenia, and depression, and significant efforts have been undertaken to develop various compounds that bind to these receptors for potential use in diagnosis and therapy of disorders associated with serotonin 5-HT1A receptors. Among other proposed approaches, particularly desirable compounds include those suitable for selective positron emission tomography (PET) analysis.

Currently known serotonin 5-HT1A receptor ligands for animal and human diagnostic imaging studies include $^{11}$C-WAY-100635 (WAY), $^{18}$F-FCWAY and $^{18}$F-MPPF. Other known compounds include those in Prior Art FIG. 1 in which (1) is WAY-100635, (2) is CPC-222, (3) is SWAY, and (4) is JWAY. Still further known ligands (which may or may not be labeled) are described in Nuclear Biology and Medicine (2000) Vol. 27, 441-447, in WO96/01656 and WO94/19026, and in U.S. Pat. Nos. 6,861,427, 6,831,084, 6,821,981, and 6,670,400. While such compounds target the serotonin 5-HT1A receptors to at least some degree, numerous difficulties nevertheless exist. Among other problems, all or almost all of the known compounds are metabolized at a relatively fast rate, and/or are eliminated from plasma in an undesirably short time. Thus, data analysis is often difficult. Still further, the synthesis of such compounds is frequently difficult to achieve in adequate yields. Moreover, where $^{18}$F is used as a radiolabel, compounds are often rendered chemically instable. Worse yet, affinity of $^{18}$F-labeled compounds to the target receptor are typically relatively low.

Thus, while numerous compositions and methods for serotonin 5-HT1A receptor ligands are known in the art, all or almost all of them suffer from one or more disadvantages. Therefore, there is still a need to provide improved compositions and methods for such ligands, especially for $^{18}$F-labeled ligands.

SUMMARY OF THE INVENTION

The present invention is directed to compounds, compositions, and methods related to synthetic ligands for the serotonin 5-HT1A receptor, wherein the ligands are most preferably radiolabeled with a label that is detectable by PET and/or SPECT. Particularly preferred ligands include substituted arylpiperazinyl compounds in which an alkyl linker is covalently bound to a tertiary amine that carries an aromatic ring and a carbonyl-bound labeling moiety.

In one aspect of the inventive subject matter, the ligand has a general structure according to Formula I Formula I

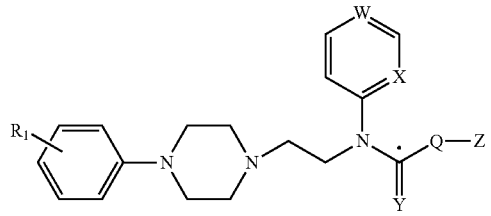

in which $R_1$ is an optionally substituted lower alkyl, alkoxy, halogen, or hydrogen, and wherein at least one carbon atom in R1 may be $^{11}$C, X and W are independently N or CH, Y is O, $NR_1$, or S, wherein * denotes an optional $^{11}$C isotope, Q is optionally substituted cycloalkyl or cycloalkenyl, and wherein Z is lower alkyl to which a PET and/or SPECT detectable label is covalently bound. In particularly preferred aspects $R_1$ is $OCH_3$ (optionally $O^{11}CH_3$), X is N, W is CH, Y is O, and the label is $^{18}$F. Still further, it is preferred that Q is cyclohexyl and Z is $CH_2$ $^{18}$F. Therefore, particularly preferred ligands include $^{18}$F-Mefway in trans- and cis-configuration as depicted in Formula IIa and Formula IIb, respectively.

Formula IIa

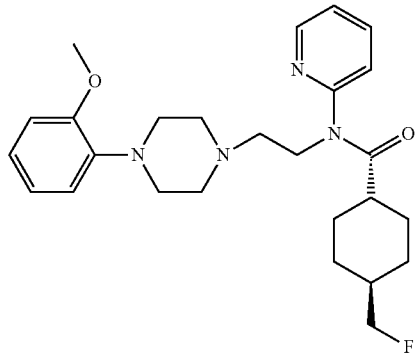

Formula IIb

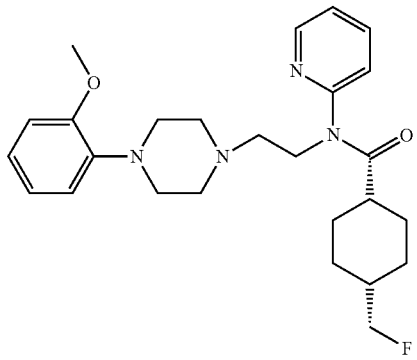

In another aspect of the inventive subject matter, a method of diagnosing or treating a disease associated with an abnormality of a serotonin 5-HT1A receptor (e.g., dysfunction, excess, or underexpression) comprises a step of administering a pharmaceutical composition that has a compound according to Formula I in a pharmaceutically acceptable carrier. Alternatively or additionally, the compound may also be administered as a prodrug or metabolite.

In a still further aspect of the inventive subject matter, methods of quantifying serotonin in a neural tissue are contemplated where a pharmaceutical composition comprising a compound according to Formula I in a pharmaceutically acceptable carrier is administered to a mammal. In a further step, a PET or SPECT scan is performed on the tissue, and the PET or SPECT signal quantity is correlated with a serotonin concentration in the tissue.

Various objects, features, aspects and advantages of the present invention will become more apparent from the following detailed description of preferred embodiments of the invention.

BRIEF DESCRIPTION OF THE DRAWING

Prior Art FIG. 1 depicts structures of exemplary known serotonin 5-HT1A receptor ligands.

DETAILED DESCRIPTION

The inventors have discovered that numerous serotonin 5-HT1A receptor ligands can be prepared that have desirable chemical and metabolic stability in vitro and in vivo, and that have relatively high and specific affinity for the serotonin 5-HT1A receptor. Typically, such ligands will be labeled using $^{18}$F, which is most preferably covalently bound to a primary carbon atom of the ligand. Furthermore, it should be appreciated that the compounds according to the inventive subject matter will typically, but not necessarily function as a receptor antagonist, and that such compounds will be particularly suitable for PET analysis.

Compounds presented herein are contemplated to be useful for diagnosis and/or treatment of various diseases associated with the serotonin 5-HT1A receptor, as well as for research and development of new drugs and/or drug-receptor interactions. Therefore, it is generally preferred that the compounds according to the inventive subject matter have a structure that (a) binds to the serotonin 5-HT1A receptor, (b) has an antagonistic effect, and/or (c) is detectable in vitro and in vivo using detection methods (most preferably based on radiation) well known in the art. Most preferably, detection of the compound in vivo and/or in vitro collocates with the location of the serotonin 5-HT1A receptor.

Figure 2:
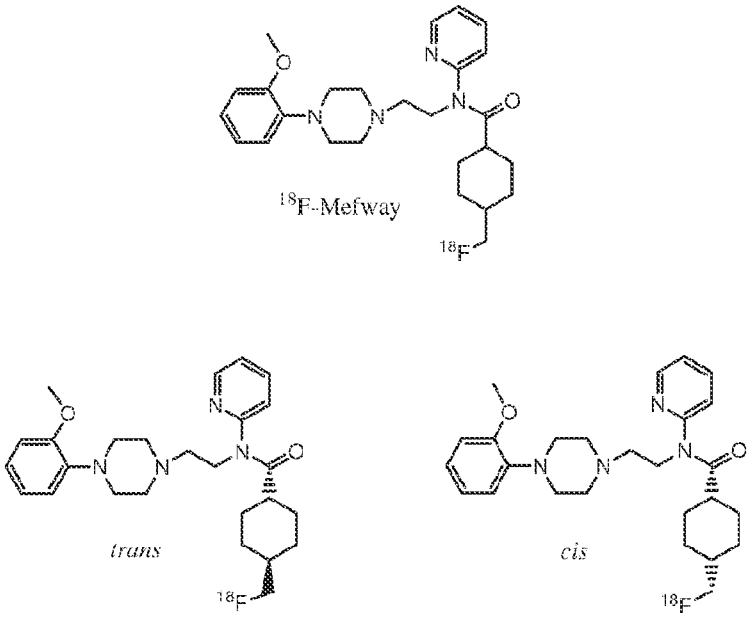
FIG. 2 depicts structures of a preferred serotonin 5-HT1A receptor ligands according to the inventive subject matter.

In one particularly preferred aspect, the serotonin 5-HT1A receptor ligand is labeled using $^{18}$F at a primary carbon atom (e.g., in a fluoromethyl group on a cyclohexyl ring). One exemplary such compound is N-(2-[4-(2-methoxyphenyl) piperazinyl]ethyl)-N-(2-pyridyl)-N-(4-18F-fluoro-methyl-cyclohexane)carboxamide (18F-Mefway), which is shown in FIG. 2. Therefore, in a more general aspect of the inventive subject matter, compositions and methods for targeting the serotonin 5-HT1A receptor are contemplated, wherein the compounds in such compositions will selectively bind to the serotonin 5-HT1A receptor and (in most instances) evoke an antagonistic effect. Preferably, where the compound is labeled using a PET detectable radio ligand (e.g., $^{11}$C or $^{18}$F), it is contemplated that binding to and/or location of the serotonin 5-HT1A receptor may be analyzed in vitro and in vivo. Moreover, such compounds may also be employed to determine the serotonin concentration in in vitro and in vivo (e.g., using competitive displacement analysis).

Especially preferred labeled compounds will include those known to selectively bind to the serotonin 5-HT1A receptor, wherein a PET detectable radio ligand is covalently bound to the compound. Typically, where the detectable radio ligand is $^{18}$F, the radio ligand is covalently bound to the compound via a primary carbon atom. Thus, contemplated compounds include those having a structure according to Formula I Formula I

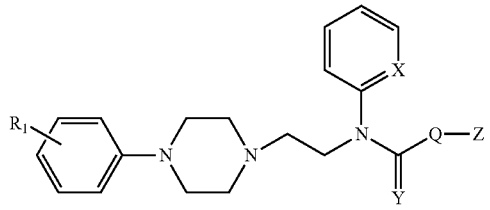

wherein $R_1$ is optionally substituted lower alkyl, alkoxy, halogen, hydroxy, or hydrogen, X is N or CH, Y is O, $NR_1$, or S, Q is optionally substituted (preferably cyclic) alkyl or alkenyl with between 1 and 8 carbon atoms, and wherein Z is lower alkyl. Where the compound is labeled, it is preferred that the radio ligand is $^{18}$F and is covalently bound to at least one of the $R_1$, Q, and/or Z group. In especially preferred aspects, the $^{18}$F label is covalently bound to a primary carbon atom. For example, suitable groups with the $^{18}$F label include R—$CH_2$ $^{18}$F, R—CHF$^{18}$F, and R—$CF_2$ $^{18}$F, wherein R may be linear, branched, or cyclic alkyl, aryl, aralkyl, various heterocyclic compounds, etc. It should further be appreciated that all isomeric forms (e.g., D-/L-isomer, cis/trans-isomer, etc., isolated or in combination) are expressly considered herein.

Particularly preferred compounds include those in which $R_1$ is $OCH_3$, in which the PET detectable label comprises $^{18}$F, and in which Q is cyclohexyl or cyclohexenyl, and Z is $CH_2$ $^{18}$F or $CH_2CH_2$ $^{18}$F. Such preferred compounds may have different stereoisomeric forms, and exemplary compounds are depicted below as Formula IIa and IIb.

Formula IIa

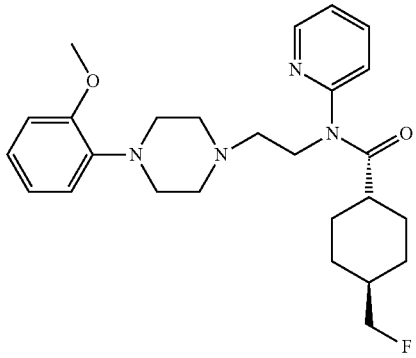

-continued

Formula IIb

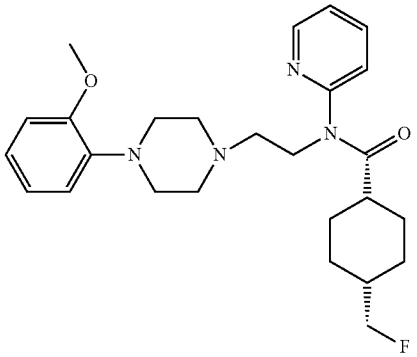

Further contemplated alternative compounds will include those in which the pyridine ring system is substituted with suitable cyclic and heterocyclic structures as shown below:

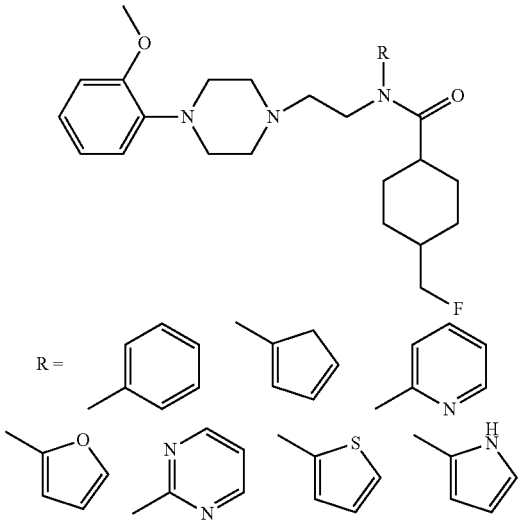

The term "alkyl" as used herein refers to a cyclic, branched, or straight hydrocarbon in which all of the carbon-carbon bonds are single bonds, and the term "lower alkyl" refers to a cyclic, branched, or straight chain alkyl of one to ten carbon atoms (e.g., methyl, ethyl, n-propyl, i-propyl, n-butyl, t-butyl, i-butyl (or 2-methylpropyl), cyclopropylmethyl, i-amyl, n-amyl, hexyl, etc.). The term "cycloalkyl" as used herein refers to a cyclic or polycyclic alkyl group containing 3 to 15 carbons. For polycyclic groups, these may be multiple condensed rings in which one of the distal rings may be aromatic (e.g., indanyl, tetrahydronaphthalene, etc.).

Similarly, the term "alkenyl" as used herein refers to an alkyl in which at least one carbon-carbon bond is a double bond. Thus, the term "lower alkenyl" includes all alkenyls with one to ten carbon atoms. The term "cycloalkenyl" as used herein refers to a cyclic or polycyclic group containing 3 to 15 carbons and at least one double bond. Likewise, the term "alkynyl" as used herein refers to an alkyl or alkenyl in which at least one carbon-carbon bond is a triple bond. Thus, the term "lower alkynyl" includes all alkynyls with one to ten carbon atoms.

As still further used herein, the term "alkoxy" refers to a —OR group, wherein R is lower alkyl, substituted lower alkyl, acyl, aryl, substituted aryl, arylalkyl, substituted arylalkyl, heteroarylalkyl, cycloalkyl, substituted cycloalkyl, cycloheteroalkyl, or optionally substituted cycloheteroalkyl.

Furthermore, the terms "aryl" and "Ar" are used interchangeably herein and refer to an aromatic carbocyclic group having at least one aromatic ring (e.g., phenyl or biphenyl) or multiple condensed rings in which at least one ring is aromatic, (e.g., 1,2,3,4-tetrahydronaphthyl, naphthyl, anthryl, or phenanthryl). Similarly, the terms "heterocycle" or "heterocyclic ring" are used interchangeably herein and refer to a saturated, partially or entirely unsaturated, or aromatic carbocyclic group having a single ring (e.g., morpholino, pyridyl or furyl) or multiple condensed rings (e.g., naphthpyridyl, quinoxalyl, quinolinyl, or indolizinyl) which include at least one heteroatom within the ring(s). The term "heteroatom" as used herein refers to an atom other than carbon (e.g., S, O, or N), which can optionally be substituted with, e.g., hydrogen, halogen, lower alkyl, alkoxy, lower alkylthio, trifluoromethyl, amino, amido, carboxyl, hydroxyl, aryl, aryloxy, heterocycle, heteroaryl, substituted heteroaryl, nitro, cyano, alkylthio, thiol, sulfamido and the like.

Still further, the term "substituted" as used herein means that a hydrogen atom that is covalently bound to a group or atom (or a free electron pair or electron pair of a double bond of an atom) is replaced by a covalently bound non-hydrogen substitutent, including hydroxyl, thiol, alkylthiol, halogen, alkoxy, amino, amido, nitro, carboxyl, cycloalkyl, heterocycle, cycloheteroalkyl, acyl, carboxyl, aryl, aryloxy, heteroaryl, arylalkyl, heteroarylalkyl, alkyl, alkenyl, alknyl, and cyano.

It should further be recognized that the compounds contemplated herein may also be active and/or prepared as a metabolites, as prodrugs, and/or otherwise modified compound, wherein the modified compound exhibits less pharmacological activity (as compared to the unmodified compound) and wherein the modified compound is converted within a target cell or target organ back into the unmodified form. For example, conversion of contemplated compounds into prodrugs may be useful where the active drug is too toxic for safe systemic administration, or where the contemplated compound is poorly absorbed by the digestive tract, or where the body breaks down the contemplated compound before reaching its target. Contemplated compounds may also be transformed by the hepatic phase I and/or phase II enzyme system, or by gastric acidity, intestinal microbial environment, or other biochemical process. Thus, suitable compounds may be oxidized, hydroxylated, ligated to a carbohydrate, etc.

Based on earlier experiments (for selected comparative data see experimental section) and published works by others, it was apparent that in vivo stability and imaging characteristics of heretofore known agents was less than desirable. Most significantly, defluorination of known compounds lead to loss in signal specificity. To improve stability, the inventors contemplated that if a labeling could be implemented that in which the labeled fluorine was covalently coupled to a primary carbon atom, stability may be improved. Still further, the inventors contemplated that if the primary labeling group could be designed to improve lipophilicity, compounds with better brain barrier penetration capability and receptor retention could possibly be achieved.

Figure 3:
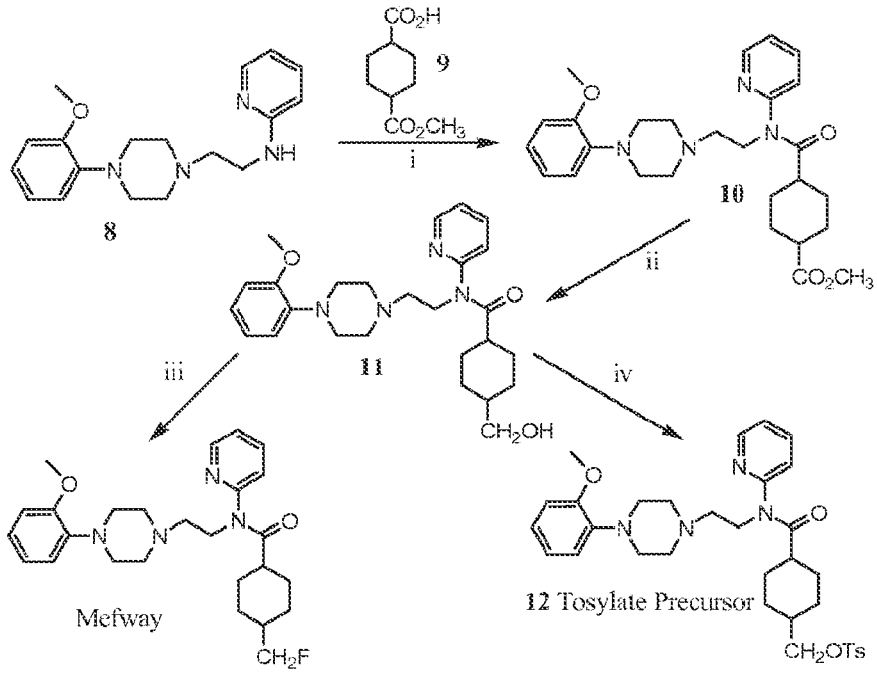
FIG. 3 depicts an exemplary synthetic pathway for a compound according to the inventive subject matter.

To that end, the inventors modified various known compounds by inclusion of $^{18}F$ into a primary carbon to thus form a fluoroalkyl-modified ligand. Among various other examples, a fluoromethyl group was added to the cyclohexyl ring of the known compounds WAY-100635 to so form mefway. Calculations and further measurements (see data below) indicated that both compounds had very similar backbone structures, suggesting that $^{18}$F-mefway would bind to the 5-HT$_{1A}$ receptor with similar characteristics as WAY-100635 thus making it a good candidate as a PET imaging agent. Remarkably, labeling on the primary carbon has improved stability to a degree that virtually no deflourination of $^{18}$F-mefway was observed in numerous in vitro and in vivo experiments. The synthesis of mefway was a three-step procedure, and the synthesis of $^{18}$F-mefway was a four-step procedure, starting from the known intermediate, WAY-100634. An exemplary synthetic route for $^{18}$F-mefway is shown in FIG. 3. Additional data and procedures for synthesis are provided in the experimental section below.

Initial and subsequent data on various compounds indicated that binding affinity and IC$_{50}$ values of mefway and WAY-100635 relative to the labeled compound $^{18}$F-mefway were similar and so provided motivation to further explore use of selected compounds for in vitro and in vivo labeling agents. A compound's lipophilicity is an important indicator of its potential in the development of a drug. Lipophilicity (quantified as a log P value) is associated with the compound's ability to interact closely with its binding site, the compound's affinity to stay bound to that site, ability to cross the blood brain barrier efficiently, and to exhibit low nonspecific binding. A measured Log P value of 2.0±0.5 has been established for high-melting polar compounds (carbamates, alcohols, amides, and ureas), and experimental Log P value of 2.62±0.06 were obtained for $^{18}$F-mefway, which is within range of optimal lipophilicity.

Especially preferred compounds (and particularly $^{18}$F-mefway) also performed well in rodent studies, and improved ratios from currently used agents were seen. Indeed, the ratios of brain region binding to cerebellum proved higher than any other reported compound when using selected compounds according to the inventive subject matter. For example, hippocampus to cerebellum ratios of 82:1, colliculus to cerebellum ratios of 46:1, and cortex to cerebellum ratios of 40:1 were measured for $^{18}$F-mefway. These specific binding ratios are substantially higher than those reported for $^{11}$C-WAY-100635, $^{18}$F-MPPF, and $^{18}$F-FCWAY. Further, WAY-100635 was able to displace binding of $^{18}$F-mefway, confirming $^{18}$F-mefway binding to the 5-HT1A receptor.

Based on such favorable binding affinity and selectivity, the inventors also contemplated use of the compounds according to the inventive subject matter for quantitative measurements of serotonin levels in the brain. Earlier experiments showed that $^{18}$F-Mefway binding to the 5-HT1A receptor is clearly and strongly inhibited by serotonin (IC$_{50}$ 169-244 nM) in various regions of the brain as evidenced by various in vitro studies. Consequently, contemplated compounds may be employed as a noninvasive imaging tool to measure absolute concentration and/or changes in brain serotonin levels. In this context, it should be noted that recent in vivo PET studies using $^{18}$F-MPPF and fenfluramine-induced serotonin release have failed to measure competition with $^{18}$F-MPPF.

Moreover, and with respect to $^{18}$F-mefway (and likely other compounds contemplated herein), uptake and retention of the labeled compound was found to be similar to that found for $^{11}$C-WAY-100635: The kinetics exhibit an approach to pseudoequilibrium around 80 mins in receptor-rich regions (e.g., hippocampus; ratio of hippocampus to cerebellum exceeded 9). Such selectivity of in vivo binding exceeds many of the binding properties of currently known 5-HT$_{1A}$ radiotracers. Moreover, several cortical regions also exhibited a high degree of binding consistent with the known distribution of 5-HT$_{1A}$ receptors. Regions such as the raphe exhibited a ratio of 3.5. These ratios compare, and even improve upon known ratios of $^{11}$C-WAY-100635 $^{18}$F-MPPF, and $^{18}$F-FCWAY. Blood analysis indicates the presence of significant amount of the parent $^{18}$F-mefway, suggesting that cerebellum may be suitable for use in reference region analysis of the binding of $^{18}$F-mefway. Preliminary distribution volume ratios in the range of 1.8 to 7 were measured for various regions and are consistent with the findings with $^{11}$C-WAY-100635.

Based on the observed and/or expected stability of contemplated compounds, it should be recognized that these compounds may be employed for various uses. Among other uses, it is contemplated that the compounds will allow the study of levels of endogenous serotonin, and will provide a tool to determine the location, function, and/or quantity of receptors in neural (and other) tissue. Thus, it is contemplated that the compounds and compositions according to the inventive subject matter are suitable for diagnostic and/or therapeutic purposes.

Consequently, a pharmaceutical composition may include at least one of contemplated compounds (preferably in oral or parenteral formulation) at a concentration effective to treat a disease associated with serotonin 5-HT1A receptor dysfunction. In preferred aspects of such compositions, the concentration is effective to provide an antagonist effect at the serotonin 5-HT1A receptor, while the disease is typically Alzheimer's disease, cognitive impairment, schizophrenia, dementia, anxiety, and/or depression. Especially contemplated methods of diagnosing a mammal having a disease associated with a serotonin 5-HT1A receptor dysfunction includes a step in which contemplated compounds are administered to the mammal (typically in a labeled form) at a dosage effective to locate and/or quantify in vivo binding of the labeled compound to the serotonin 5-HT1A receptor. Preferably, the label is a isotope suitable for detecting the compound in vivo using PET (preferably $^{18}$F), and contemplated compounds are parenterally administered. Further especially suitable uses and compositions useful for contemplated compounds presented herein are those disclosed in WO 2005/1212796, which is incorporated by reference herein.

Particularly preferred compositions according to the inventive subject matter may be administered using various routes, including orally, parenterally, by inhalation, topically, rectally, nasally, or via an implanted reservoir, wherein the term "parenteral" as used herein includes subcutaneous, intravenous, intramuscular, intraarticular, intrasynovial, intrathecal, intrahepatic, intralesional, and intracranial administration (typically injection or infusion). Preferably, the compositions are administered orally, intraperitoneally, or intravenously. Compositions according to the inventive subject matter may further be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

With respect to the amount of contemplated compounds in the composition, it should be recognized that the particular quantity will typically depend on the specific formulation, active ingredient, and desired purpose. Therefore, it should be recognized that the amount of contemplated compounds will vary significantly. However, it is generally preferred that the compounds are present in a minimum amount effective to deliver a therapeutic effect and/or to be visualized in vitro and/or in vivo.

Thus, in most preferred embodiments, contemplated compounds will be present in an amount of between about 0.1 ng/ml to about 100 mg/ml, more typically in an amount of between about 10 ng/ml to about 10 mg/ml, and most typically between about 1 μg/ml to about 100 μg/ml. Where the formulation is a solid, contemplated compounds will be present in an amount of between about 0.1 ng/g to about 100 mg/g, more typically in an amount of between about 10 ng/g to about 10 mg/g, and most typically between about 1 μg/g to about 100 μg/g. With respect to a dosage unit, it is generally contemplated that contemplated compounds are administered at a dosage effective to achieve a desired therapeutic effect or at a dosage effective to provide visualization in vitro and/or in vivo.

Therefore, suitable amounts of contemplated compounds will be in the range of 0.1 μg per dosage unit to about 0.5 gram per dosage unit, more typically between 10 μg per dosage unit to about 0.05 gram per dosage unit, and most typically between 50 μg per dosage unit to about 100 mg per dosage unit. Thus, suitable dosages will be in the range of about 0.01 μg/kg and 100 mg/kg, more typically between 1 μg/kg and 50 mg/kg, and most typically between 10 μg/kg and 10 mg/kg.

With respect to suitable labeling amounts, it is generally contemplated that all quantities are deemed suitable that can be detected using an in vitro and/or in vivo imaging technology, and particularly in vivo PET. Typically, a radiolabeling precursor compound will be labeled with a fluorine-18 source by an imaging center. For example, several microcuries to several millicuries will be produced and then used for imaging studies. Therefore, contemplated compounds and kits may also be include at least one of a precursor molecule, the labeling molecule containing $^{18}F$, and the $^{18}F$ labeled ligand.

Experiments

All chemicals and solvents were of analytical or HPLC grade from Aldrich Chemical Co. and Fisher Scientific. Cis- and Trans-Cyclohexane-1,4-dicarboxylic acid monomethyl ester was purchased from Rieke Metals, Inc (Lincoln, Nebr.) and cis-trans mixture was purchased from CNH Technologies (Woburn, Mass.). WAY-100635 was synthesized using reported procedures (Pike et al., 1995). Electrospray mass spectra were obtained on a Model 7250 mass spectrometer (Micromass LCT). Proton NMR spectra were recorded on a Bruker OMEGA 500 MHz spectrometer.

Analytical thin layer chromatography (TLC) was carried out on silica coated plates (Baker-Flex, Phillipsburg, N.J.). Chromatographic separations were carried out on preparative TLC (silica gel GF 20×20 cm 2000 micron thick; Alltech Assoc. Inc., Deerfield, Ill.) or silica gel flash column or semi-preparative reverse-phase columns using the Gilson high performance liquid chromatography (HPLC) systems.

High specific activity $^{18}F$-fluoride was produced in the MC-17 cyclotron or the CTI RDS-112 cyclotron using oxygen-18 enriched water ($^{18}O$ to $^{18}F$ using p, n reaction). The high specific activity $^{18}F$-fluoride was used in subsequent reactions which were carried out in automated radiosynthesis units (either a chemistry processing control unit (CPCU or a nuclear interface fluorine-18 module). Fluorine-18 radioactivity was counted in a Capintec dose calibrator while low level counting was carried out in a well-counter (Cobra quantum, Packard Instruments Co., Boston, Mass.). Radioactive thin layer chromatographs were obtained by scanning in a Bioscan system 200 Imaging scanner (Bioscan, Inc., Washington, D.C.).

Rat brain slices were obtained on a Leica 1850 cryotome. Fluorine-18 autoradiographic studies were carried out by exposing tissue samples on storage phosphor screens. The apposed phosphor screens were read and analyzed by OptiQuant acquisition and analysis program of the Cyclone Storage Phosphor System (Packard Instruments Co., Boston, Mass.). Monkey PET were carried out using a high-resolution ECAT EXACT HR+ scanner. All animal studies were approved by the Institutional Animal Care and Use Committee of University of California-Irvine and Wright State University, Dayton, Ohio.

Synthesis

An exemplary synthetic mute for mefway is shown in FIG. 3. Reaction of WAY-100634, (8) with the commercially available cis- or trans-cyclohexane-1,4-dicarboxylic acid monomethyl ester was carried out using BOP to provide N-{2-[4-(2-methoxyphenyl)piperazine-yl]ethyl}-N-(2-pyridyl)-N-(4-carboxymethylcyclohexane)carboxamide (10). The yields of this coupling step were moderate (30-40%); acid chloride procedure as described for the synthesis of WAY-100635 may provide higher yields. This ester (10) was reduced with $LiAlH_4$ more efficiently than with $NaBH_4$, although in both cases there was significant breakdown of the amide bond. Conversion of the alcohol to the corresponding fluoro-compound (mefway) proceeded in high yields smoothly (>80%). The alcohol (11) was converted to the tosylate (12) in approximately 50% yield.

N-{2-[4-(2-methoxyphenyl)piperazinyl]ethyl}-N-(2-pyridyl)-N-(4-carboxymethylcyclo-hexane)-carboxamide (10): Using reported procedures, 1-(2-Methoxyphenyl)-4-(2-(2-pyridylamino)ethyl)-piperazine (WAY-100634, 8, Pike et al., 1995) (96.3 mg, 0.3 mmol) was reacted with 4-carbomethoxycyclohexane-1-carboxylic acid (9, 47.4 mg, 0.3 mmol) in the presence of benzotriazol-1-yloxytris(dimethylamino)phosphonium hexafluorophosphate (BOP; 132.0 mg, 0.3 mmol), triethylamine (125 μL), and $CH_3CN$ (1.5 mL). The mixture was stirred at room temperature for 24 hours. Solvent was removed by rotary evaporation. The residue was then taken up in water (3 mL) and extracted with dichloromethane. The extracts were concentrated and purified on preparative TLC($CH_2Cl_2$:$CH_3OH$, 9:1). $^1$H-NMR (500 MHz, $CDCl_3$) δ ppm: trans-isomer: 8.52-8.53 (dd, 1H), 7.76-7.79 (dt, 1H), 7.25-7.31 (m, 2H), 7.02-6.97 (m, 1H), 6.91-6.87 (m, 2H), 6.83-6.85 (m, 1H), 3.97-4.0 (t, 2H), 3.84 (s, 3H, $OCH_3$), 3.62 (s, 3H, $CO_2CH_3$), 3.02 (br, 4H), 2.63-2.66 (m, 6H), 2.29-2.32 (m, 1H), 2.04-2.08 (m, 1H), 1.84-1.95 (m, 4H), 1.07-1.64 (m, 4H). MS, m/z, 481 (30%, $[M+H]^+$), 503 (10%, $[M+Na]^+$).

N-{2-[4-(2-methoxyphenyl)piperazinyl]ethyl}-N-(2-pyridyl)-N-(4-hydroxymethylcyclo-hexane)-carboxamide (11): The ester (10) (4.8 mg; 0.01 mmol) was treated with a small amount (0.1 mL of 1M THF solution; 0.1 mmol) of $LiAlH_4$ in an ice bath for 30 minutes. The mixture was allowed to stir subsequently at ambient temperature for 30 mins. Excess $LiAlH_4$ was quenched with saturated ammonium chloride and solvents were removed by rotary evaporation. The residue was extracted with $CH_2Cl_2$ and purified by silica preparative TLC plate (9:1 $CH_2Cl_2$:$CH_3OH$) to provide N-{2-[4-(2-methoxyphenyl)piperazinyl]ethyl}-N-(2-pyridyl)-N-(4-hydroxymethylcyclohexane)carboxamide (11) was a sticky oil. $^1$H-NMR (500 MHz, $CDCl_3$) δ ppm: trans-isomer: 8.52-8.53 (dd, 1H), 7.75-7.78 (dt, 1H), 7.24-7.32 (m, 2H), 7.00-6.97 (m, 1H), 6.91-6.87 (m, 2H), 6.83-6.85 (m, 1H), 4.0 (br, 2H), 3.84 (s, 3H, $OCH_3$), 3.39 (d, 2H, —$CH_2O$—), 3.0 (br, 4H), 2.64 (m, 6H), 2.20 (m, 1H), 1.76-1.86 (m, 4H), 0.75-1.64 (m, 5H). MS, m/z, 453 (30%, $[M+H]^+$).

N-{2-[4-(2-methoxyphenyl)piperazinyl]ethyl}-N-(2-pyridyl)-N-(4-fluoromethylcyclo-hexane)-carboxamide: The alcohol (11) (4.5 mg; 0.01 mmol) was also treated with diethylaminosulfur trifloride (DAST) (2 μL; 0.015 mmol) in $CH_2Cl_2$ (0.5 mL) while cooled in a an ice-water bath. The reaction mixture was allowed to warm up to ambient temperature and stirred for 24 hours. The reaction mixture was washed with 10% $NaHCO_3$ followed by water. The $CH_2Cl_2$ was dried over $MgSO_4$, filtered and removed by rotary evaporation. After purification by silica preparative TLC plate (9:1 $CH_2Cl_2$:$CH_3OH$) N-{2-[4-(2-methoxyphenyl)-piperazinyl]ethyl}-N-(2-pyridyl)-N-(4-fluoromethylcyclohexane)carboxamide was obtained. MS, m/z, 455 (35%, $[M+H]^+$).

N-{2-[4-(2-methoxyphenyl)piperazinyl]ethyl}-N-(2-pyridyl)-N-(4-tosyloxymethylcyclo-hexane)-carboxamide (12): The alcohol (11) (7 mg; 0.015 mmol) was reacted with p-toluenesulfonyl chloride (3.5 mg) in the presence of 2.2 μL $Et_3N$ in 0.5 mL $CH_2Cl_2$ for 24 hours at room temperature. Solvent was removed by rotary evaporation. Dichloromethane was added and washed with $NaHCO_3$ and $H_2O$. The organic layer was removed, dried with $MgSO_4$, and filtered to give N-{2-[4-(2-methoxyphenyl)piperazinyl]ethyl}-N-(2-pyridyl)-N-(4-tosyloxymethylcyclohexane)carboxamide which was purified by silica preparative TLC plate ($CH_2Cl_2$:$CH_3OH$, 9:1) (12). $^1$H-NMR (500 MHz, $CDCl_3$) δ ppm: trans-isomer: 8.52 (d, 1H), 7.73-7.79 (m, 4H), 7.30-7.35 (m, 4H), 6.99 (br, 1H), 6.84-6.90 (m, 2H), 3.96 (br 2H), 3.84 (s, 3H, $OCH_3$), 3.75 (d, 2H, —$CH_2OSO_2$—), 2.98 (br, 4H), 2.61 (m, 6H), 2.44 (s, 3H, $CH_3$), 2.10-2.20 (m, 1H), 1.85-0.80 (m, 8H). MS, m/z, 607 (20%, $[M+H]^+$).

Radiochemistry

Figure 4:
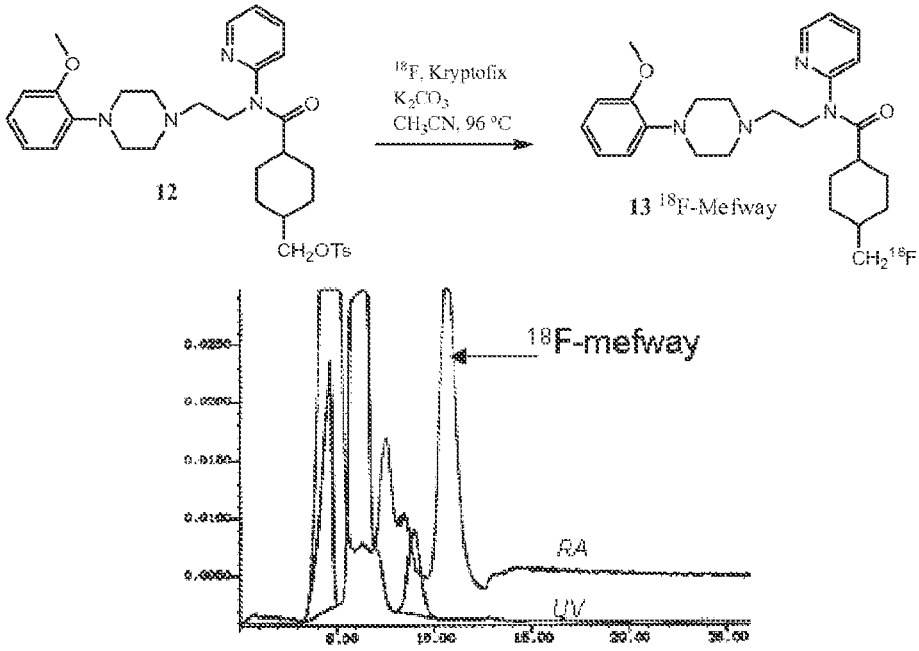
FIG. 4 depicts an exemplary radio-labeling pathways for a compound according to the inventive subject matter.

FIG. 4 illustrates the reaction of the tosylate (12) in acetonitrile with $^{18}$F-fluoride from a MC-17 cyclotron using Kryptofix and $K_2CO_3$ at 96° C. for 30 min in the CPCU proceeded efficiently, to provide $^{18}$F-mefway in a single step with a radiochemical yield of (20-30%). Semi-Preparative HPLC chromatogram separation of $^{18}$F-mefway, 13 product mixture gave the product radioactive peak at approximately 10.5 mins as seen in the HPLC chromatogram of FIG. 4. Radiochemical yields were lower than typically observed with tosylate-to-fluorine-18 exchange reactions as previously reported (Mukherjee et al., 1995). Stability of the product to the basic radiolabeling conditions (such as cleavage of the amide bond) needs further investigations. The specific activity of $^{18}$F-mefway was approximately 74-111 GBq/μmol. Alternative leaving groups may include Cl, Br, I, O-mesylate, O-tosylate, O-nosylate, O-brosylate, or other leaving groups.

The radiosynthesis of $^{18}$F-mefway was carried out using an automated synthesis procedure which employs a chemistry processing computer unit (CPCU). Fluorine-18 in $H_2$ $^{18}O$ from a MC-17 cyclotron was passed through a QMA-light sep-pak (Waters Corp. Milford, Mass.), preconditioned with 3 mL of $K_2CO_3$, 140 mg/mL, followed by 3 mL of anhydrous acetonitrile. The fluorine-18 trapped in the QMA-light sep-pak was then eluted (using nitrogen gas) with 1 mL Kryptofix222/$K_2CO_3$ (360 mg/75 mg in 1 mL of water and 24 mL of acetonitrile) and transferred to the CPCU reaction vessel. The "SYNTHI" program in the CPCU was used for the synthesis. This involved initial drying of the $^{18}$F-fluoride, Kryptofix, and $K_2CO_3$ mixture at 120° C. for 10 mins. Subsequently, acetonitrile (2 mL) from CPCU reagent vial #2 was added and evaporated at 120° C. for 7 mins to ensure dryness of the $^{18}$F-fluoride mixture. Following this, the precursor, N-{2-[4-(2-methoxyphenyl)piperazinyl]ethyl}-N-(2-pyridyl)-N-(4-tosyloxymethyl-cyclohexane)carboxamide, 12 (1-2 mg in 0.5 mL of anhydrous acetonitrile continued in CPCU reagent vial #3) was added and the reaction went for 15 to 30 min at 96° C. Subsequent to the reaction, $CH_3OH$ (7 mL contained in CPCU reagent vial #4) was added to the mixture and the $CH_3OH$ contents were passed through a neutral alumina sep-pak (prewashed with methanol in order to remove any unreacted $^{18}$F-fluoride. The collected $CH_3OH$ solution coming out of the CPCU now contained N-{2-[4-(2-methoxyphenyl)piperazinyl]ethyl}-N-(2-pyridyl)-N-(4-$^{18}$F-fluoromethylcyclohexane)carboxamide, 13 ($^{18}$F-mefway). The $CH_3OH$ was removed in vacuo and the residue was taken up for HPLC purification. Product was purified in a reverse-phase HPLC C-18 column with 60% acetonitrile: 40% water containing 0.1% triethylamine with a flow rate of 2.5 mL/min. Semi-Preparative HPLC separation of the $^{18}$F-mefway was performed and specific activity was measured. The retention time of $^{18}$F-mefway was found to be 10.5 minutes (FIG. 4, HPLC chromatogram). The $^{18}$F-mefway fraction was collected into a flask and the solvent was removed in vacuo using a rotary evaporator. The radiosynthesis was accomplished in 2 hrs with an overall radiochemical yield of 20-30% decay corrected. Specific activity was measure to be 74-111 GBq/μmol.

This collected fraction was taken to near dryness in vacuo. Approximately 5-8 mL of sterile saline (0.9%, NaCl INJ, USP, 10 mL single-dose, Abbot Laboratories, Chicago, Ill.) was added to the flask. The contents of the flask were then drawn into a 5 or 10 mL sterile syringe depending on volume. The contents of the syringe were then filtered through a 0.2 micron Millex-FG Millipore sterile filter (Millipore Corp., Bedford, Mass.). This final dose was then used for in vitro and in vivo studies.

Trans- and Cis-Mefway

Since it may be assumed that cis- and trans-isomers may have different in vitro and in vivo properties, independent synthesis and evaluation was performed. Such synthesis and analysis was prompted by the recognition that cis-18F-FCWAY and trans-18F-FCWAY had distinct properties.

The two acids, trans-4-carbomethoxycyclohexane-1-carboxylic acid and cis-4-carbometh-oxycyclohexane-1-carboxylic acid were purchased from Rieke Specialty Compounds, Rieke Metals Inc. Electrospray mass spectra were obtained on a Model 7250 mass spectrometer (Micromass LCT) which provided mass peaks of [M+H]=187 and [M+Na]=209 for both isomers. Proton NMR spectra were recorded on a Bruker OMEGA 500 MHz spectrometer of the two isomers to confirm purity. The trans-isomer exhibits a greater upfield shift of the β-methylene adjacent to the carboxylic acid (δ=1.71 ppm for cis- and 1.47 ppm for trans-). The acids were converted to the respective trans- and cis-4-carbomethoxycyclohexane-1-carbonyl chloride (see below) by heating with excess of thionyl chloride (approx. 5-fold molar equiv) at 50° C. for 3 hours. The excess thionyl chloride was removed under vacuo to provide the respective acid chlorides for use in the next step of formation of the amide. The Synthesis of trans- and cis-4-carbomethoxycyclohexane-1-carbonyl chloride is shown below:

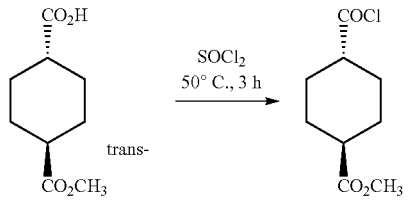

-continued

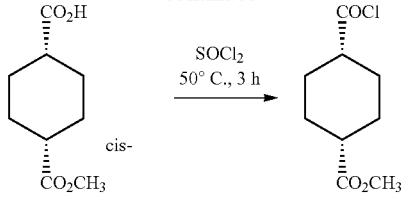

Synthesis of the mefway isomers was then carried out as shown further below. In our original procedure, we used benzotriazol-1-yloxytris(dimethylamino)phosphonium hexafluoro-phosphate (BOP) as a condensing agent for the piperazineamine or WAY-100634 and the acid. The yields of this coupling reaction were around 40%. In order to enhance this yield we have used the acid chlorides instead. This step in the synthesis of WAY-100635 has been carried out using cyclohexanecarbonyl chloride in high yields. The next step involves conversion of the ester to an alcohol. Sodium borohydride and diisobutylaluminum hydride did not provide optimal conditions for reduction. Thus far, lithium aluminum hydride seemed to work better at low temperature, however, there is still a significant loss of the starting material as a result of amide bond cleavage. Nonetheless, this reduction gave approx. 30-35% yield as previously reported. This alcohol is a key intermediate both for the synthesis of mefway as well as the synthesis of the precursor for radiolabeling (tosylate, mesylate, halides, or other leaving groups). The alcohol was treated with one molar equivalent of diethylaminosulfur trifluoride (DAST) in dichloromethane while cooled in an ice-water bath. The reaction mixture was allowed to warm up to ambient temperature and stirred for 24 hours. The alcohol will also be reacted with p-toluenesulfonyl chloride in the presence of triethylamine in dichloromethane for 24 hours at room temperature.

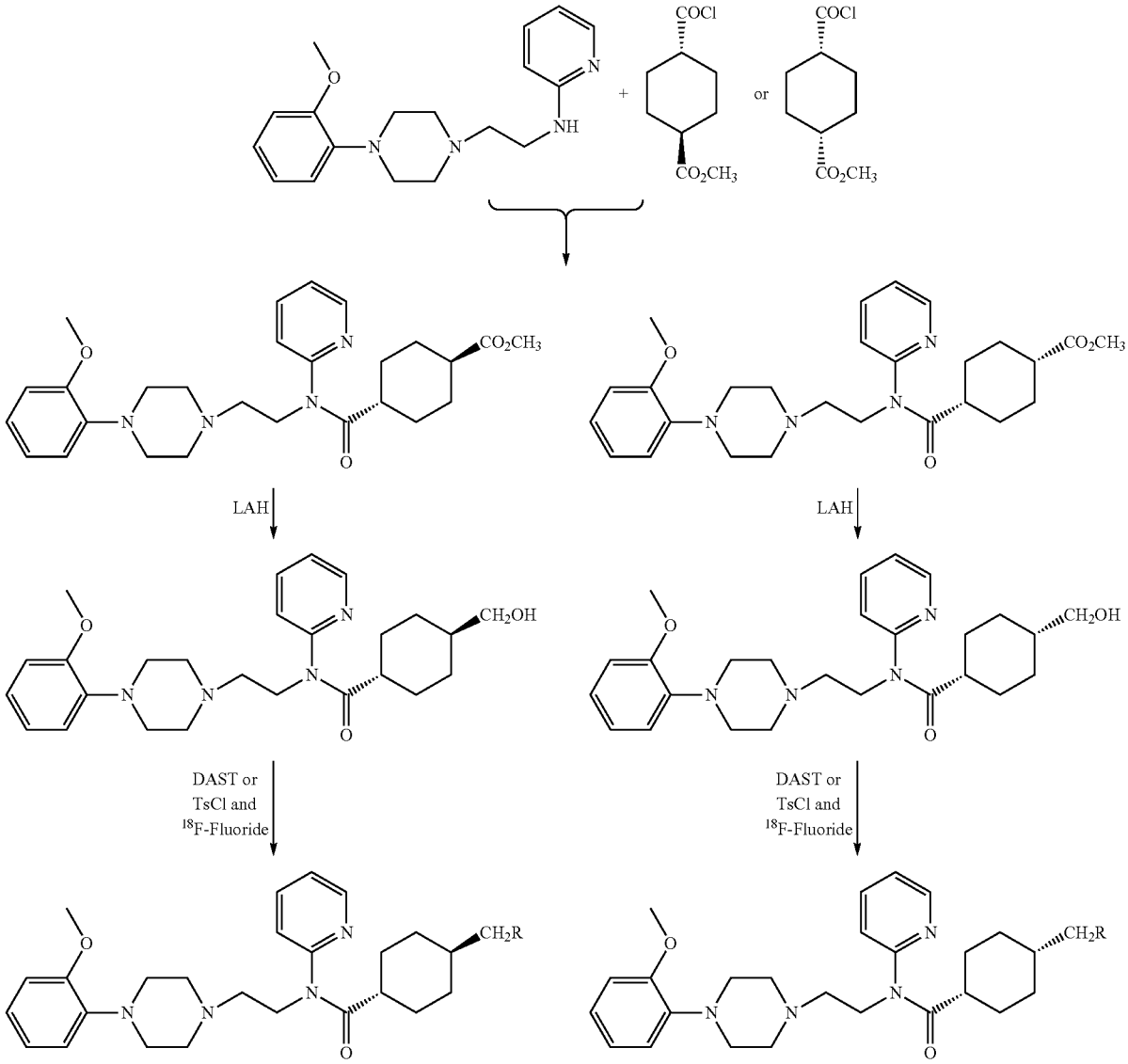

R = F for Mefway or OTs for labeling precursor or $^{18}F$ for $^{18}F$-Mefway

High specific activity $^{18}$F-fluoride was produced in the MC-17 cyclotron using oxygen-18 enriched water ($^{18}$O to $^{18}$F using p, n reaction). This $^{18}$F-fluoride was used in subsequent reactions in automated chemistry processing control unit (CPCU). Fluorine-18 radioactivity was counted in a Capintec dose calibrator while low level counting was done in a well-counter (Cobra quantum, Packard Instruments Co). The mefway precursor molecule, tosylate or mesylate was reacted with $^{18}$F-fluoride in an automated synthesis unit. The methanolic solution of product, $^{18}$F-mefway was purified in a reverse-phase HPLC $C_{18}$ Econosil colunm 250×10 mm (Alltech Assoc. Inc.) with 60% acetonitrile: 40% water containing 0.1% triethylamine with a flow rate of 2.5 mL/min. The retention time of trans-$^{18}$F-mefway was expected to be approx. 10.5 minutes. The radiosynthesis and purification was complete in 1.5 hrs. The yield of $^{18}$F-mefway was in the range of 20-30% decay corrected.

$^{11}$Carbon Labeled Trans- and Cis-Mefway

It is generally noted that carbon-11 labeled radiotracers have a potential advantage of back-to-back same day studies. This can be of value when pharmacological or behavioral challenges are being studied. It can avoid movement of the subject from the PET scanner. Also, if drug effects are being explored, then repeat studies can be performed within two to three hours of the first study. This is typically not the case of fluorine-18 labeled radiotracers. It will generally take an overnight wait to repeat a study with fluorine-18. Carbon-11 radiotracers allow good imaging statistics only for about an hour to 90 minutes. Thus, the radiotracer ought to achieve optimal binding kinetics within this time period. In the case of mefway, optimal binding kinetics may be achieved in 90 minutes in the various brain regions. Formula IIIa and IIIb below illustrate exemplary labeling with O-$^{11}$C-methoxy group labeling and Carbonyl-$^{11}$C-labeling, respectively.

Formula IIIa

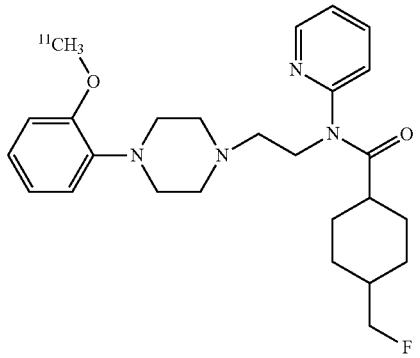

Formula IIIb

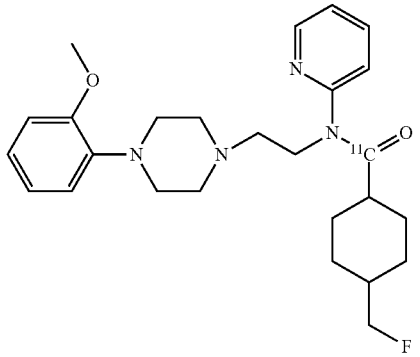

In Vitro Binding Affinity

In vitro binding affinity of WAY-100635 and mefway to 5-HT$_{1A}$ receptor sites was determined from a competitive binding assay using $^{18}$F-mefway as the radioligand. In vitro binding affinity of mefway was measured in rat brain slices labeled with fluorine-18. The brains from Sprague-Dawley rats were extracted and frozen in isopentane at −20° C. Several 10 μm thick horizontal rat brain slices were pre-incubated at room temperature for 15 minutes in 50 mM Tris-HCl buffer (pH 7.4). The horizontal slides were then treated with increasing concentrations of WAY-100635 and mefway in the presence of 167 kBq/mL of $^{18}$F-mefway at 37° C. for 1 hour. After incubation slides were washed twice with cold buffer for one minute, dipped in cold water, air dried, and exposed to phosphor storage screens for 24 hours. Autoradiographs were generated using the Packard Phosphor Cyclone Imager, and the apposed phosphor screens were read by the Cyclone Storage Phosphor System. To calculate binding affinity of WAY and mefway to 5-HT1A receptor sites, the non-specific binding was subtracted from all samples and changes in specific binding under different concentrations of WAY-100635 and mefway was calculated. Binding affinity ($IC_{50}$) was calculated using KELL program (BioSoft Inc).

Both WAY-100635 and mefway bound to the 5-HT$_{1A}$ receptor site and prevented binding of $^{18}$F-mefway. As WAY-100635 and mefway reached micromolar concentrations the amount of $^{18}$F-mefway bound to the 5-HT$_{1A}$ receptors was below 5% in all brain regions. Binding affinity ($IC_{50}$) of WAY-100635 and unlabeled mefway against $^{18}$F-mefway was measured. Mefway and WAY-100635 both showed an approximately equal decrease in binding of $^{18}$F-mefway. Mefway exhibited an $IC_{50}$ of 32.1±2.4 nM which was similar to the affinity of WAY-100535, $IC_{50}$ of 23.2±2.8 nM.

Lipophilicity

Lipophilicity (log P) was measured to evaluate lipid solubility of $^{18}$F-mefway. The lipophilicity was measured by partitioning between n-octanol and 50 M Tris-HCl (pH 7.4) buffer. Into three tubes 2 mL of n-octanol and 2 mL of buffer were added and vortexed. To this mixture 370 kBq of $^{18}$F-mefway was added. The mixture was again vortexed and allowed to settle. The layers were separated and the aqueous layer was centrifuged again to remove n-octanol contamination. An aliquot of both layers was counted for concentration of $^{18}$F-mefway using the Cobra Quantum well counter (Packard Instruments Co., Boston, Mass.). Log P was taken as the concentration of $^{18}$F-mefway in n-octanol over concentration of buffer.

Lipophilicity (Log P) of $^{18}$F-mefway measured between n-octanol and a 50 M Tris-HCl (pH 7.4) buffer was found to be 2.62±0.06. This compares well to the reported log P of $^{11}$C-WAY-100635 and $^{11}$C-Desmethyl WAY-100635. These values also suggest that $^{18}$F-mefway would demonstrate good brain penetration.

In Vitro Autoradiographic Studies

Male Sprague-Dawley rats (200-250 g) were anesthetized and decapitated, the brain was rapidly removed and frozen in isopentane at −20° C. Horizontal slices were cut 10 μm thick using a Leica 1850 cryotome. Slices contained the regions of cortex, hippocampus, and other regions known to contain 5-HT$_{1A}$ receptors. Brain slices were stored at −20° C. Brain slices were preincubated in 50 mM Tris-HCl buffer (pH 7.4) for 10 mins. The slices were then incubated with 130-148 kBq/mL of $^{18}$F-mefway at 37° C. for 1 hr. Nonspecific binding was measured in the presence of 10 μM of WAY-100635. For serotonin studies increasing amounts of serotonin (1 nM to 10 μM) competed with 130-148 kBq/mL of $^{18}$F-mefway at 37° C. for 1 hr. After incubation, slides were washed twice (one minute for both washes) with ice-cold buffer. Slides were then quickly dipped in cold deionized water, air dried, and exposed to a phosphor screen for 24 hours. The autoradiographs were generated using the Phosphor Cyclone Imager (Packard Instruments Co., Boston Mass.). The amount of binding was evaluated in digital light units (DLU/mm$^2$) using OptiQuant accusation and analysis program (Packard Instruments Co.) Autoradiographs were quantified using a computer-based image analysis system (OptiQuant Version 4.0 Packard Instruments Co., Boston Mass.).

Figure 5:
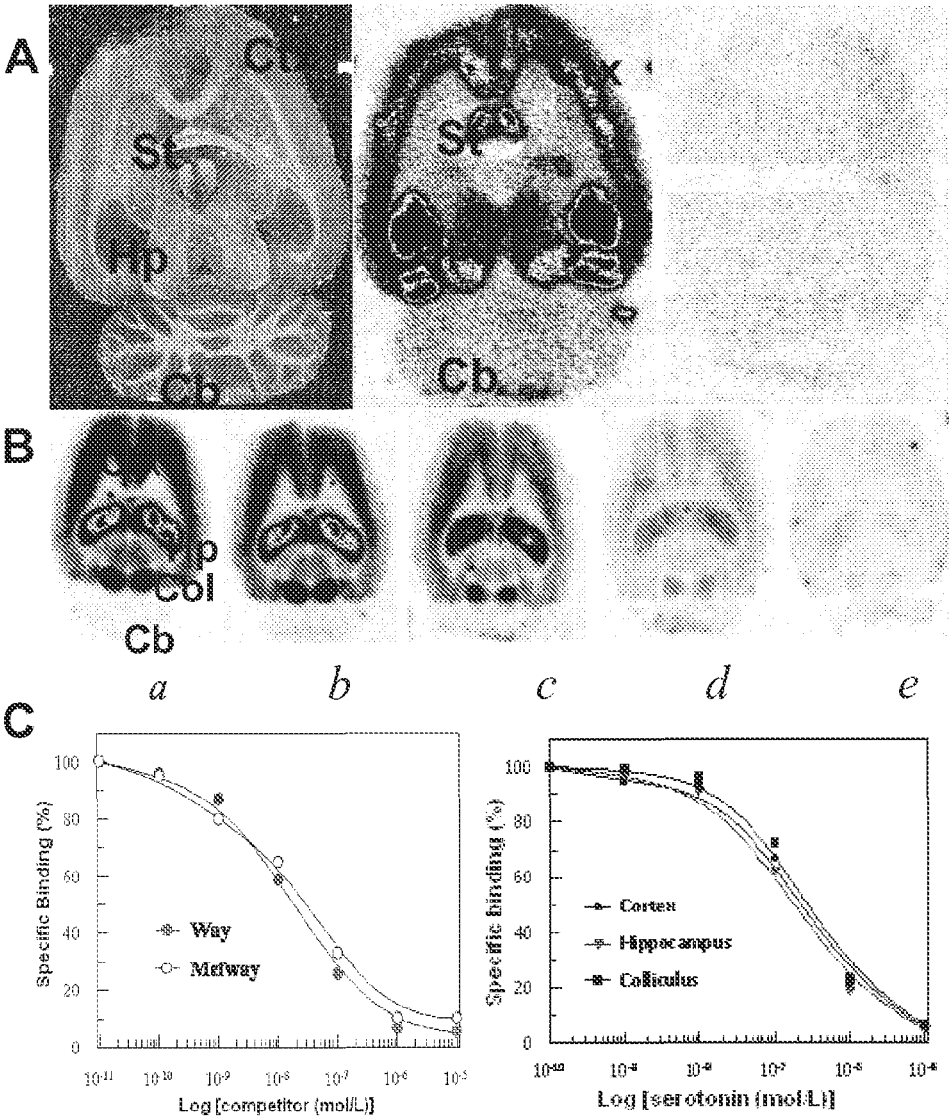
FIG. 5 depicts binding of $^{18}$F-mefway in the rat brain.

FIG. 5 illustrates In vitro horizontal brain slices of rat brain showing binding of $^{18}$F-mefway (red=highest binding and white=lowest binding; Ctx: cortex; Hp: hippocampus; St: striata; Cb: cerebellum); Left: image shows rat brain slice, 10 μm thick, showing brain regions; Center: same slice after treatment with 130-148 kBq/mL of $^{18}$F-mefway; Right: rat brain slice with nonspecific binding—in the presence of 10 μM of WAY-100635. (B). Horizontal rat brain slices (with dorsal hippocampus) showing in vitro binding in a competitive study of $^{18}$F-mefway with increasing concentrations of serotonin (5HT; a: 1 nmol/L; b: 10 nmol/L; c: 100 nmol/L; d: 1 tμmol/L; e: 10 μmol/L)(Ctx: cortex; Hp: hippocampus; Col: colliculus; Cb: cerebellum). (C). Left: Competition curves of WAY-100635 and mefway against $^{18}$F-mefway measured autoradiographically in the hippocampus of rat brain slices. Inhibition constant, $IC_{50}$, of WAY-100635=23.2±2.8 nM and Mefway=25.7±2.4 nM; Right: Inhibition curves of $^{18}$F-mefway binding by serotonin measured autoradiographically in different brain regions of rat brain slices (shown in B).

Competition Study of Serotonin with $^{18}$F-Mefway

Serotonin competition was studied in increasing concentrations 1 nM, 10 nM, 100 nM, 1 μM, and 10 μM. It was found with increasing concentrations of serotonin there was a decrease in the amount of $^{18}$F-mefway binding to the 5-HT1Areceptor. This supports the idea that mefway is inhibited by serotonin in the brain. Differing levels of serotonin allowed for the calculation of $IC_{50}$ values. An $IC_{50}$ value for serotonin was calculated for all three brain regions. Colliculus gave the highest $IC_{50}$ value, 243.5±2.0 nM. Hippocampus and cortex, gave values of 169.4±5.0 and 218.3±15. It was found that serotonin displaced >85% in hippocampus and >70% in cortex of $^{18}$F-mefway binding.

Rodent Studies with Trans-$^{18}$F-Mefway

Figure 7:
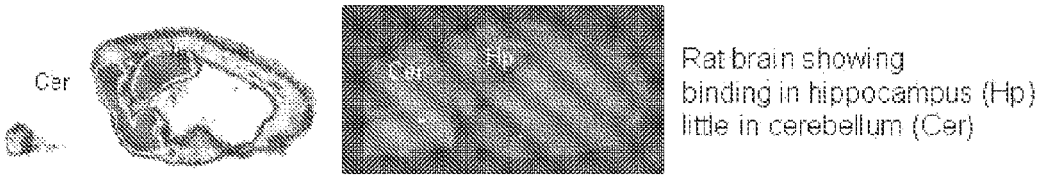
FIG. 7 depicts binding of trans-$^{18}$F-mefway binding in rat brain.

Binding of trans-$^{18}$F-mefway was evident in several 5HT1A receptor-rich regions, including hippocampus and cortex. Using cerebellum as a reference region, rat brain slices gave ratios of hippocampus/cerebellum=55 and cortex/cerebellum=17. Studies in transgenic mouse models of Alzheimer's disease show >90% loss in 5HT1a receptor binding (data not shown). Exemplary results are shown in FIG. 7 in which trans-$^{18}$F-Mefway binding to serotonin 5HT1A receptors is depicted in rodent brain.

Monkey PET Study

In vivo studies were performed in a Rhesus monkey. The monkey was anesthetized using ketamine (10 mg/kg) and xylazine (0.5 mg/kg) and maintained on 1-1.5% isoflurane. Two intravenous catheters were placed, one on each arm, for administration of the radiopharmaceutical and for obtaining blood samples during the study. Vital signs of the money were monitored carefully. The monkey did not show any unusual deviations from baseline values. The head of the animal was placed in the gantry of an ECAT EXACT HR+PET scanner and positioned in place with the use of adhesive tape. A transmission scan using a Ge-68/Ga-68 rod source was acquired prior to administration of the radiopharmaceutical to correct for tissue attenuation of the coincident radiation. A dynamic sequence of scans was acquired for 180 minutes after administration of 130 MBq of $^{18}$F-Mefway intravenously (specific activity=74-111 GBq/μmol). Data in the final form were expressed in units of percent-injected dose/mL or kBq/mL. Areas showing maximal radioligand binding in the frontal cortex, temporal cortex, dorsal raphe and other braain regions were delineated in the images. The PET images were coregistered with an MRI image template of the rhesus monkey in order to provide anatomical detail as reported previously. This MRI template of the rhesus (Macaca mulatta) brain is an average of 6 monkeys with T1-weighted MR scans. PET image summed till 120 min duration was used for the coregistration. Coregistration of the PET-MR data was carried out by VINCI program (CPS Innovations, Inc.). Time activity curves were obtained for all of these regions.

A blood analysis of the monkey PET study subsequent to administration of $^{18}$F-mefway was performed to observe levels of breakdown in the blood similar to methods described for $^{18}$F-fallypride. Venous whole blood (approx. 1 mL) was obtained at various time-points (5, 10, 15, 30, 45, 60, 90, 120, 150 and 180 min) during the course of the PET study. The samples were centrifuged in a Microfuge centrifuge (Eppendorf Centrifuge 5415C) at 12,000 rpm for 5 min. Plasma, 0.6 mL was separated from each sample and 0.1 mL was counted from each sample. was extracted. The remaining 0.5 mL of plasma at each time point was combined with 0.1 mL $NaHCO_3$ and mixed well and subsequently extracted with 0.4 mL of ethyl acetate. The ethyl acetate was separated and 0.1 mL of ethyl acetate layer and 0.1 mL of aqueous layer were counted for analysis of $^{18}$F-mefway in blood. The aqueous layer contains hydrophilic metabolites of $^{18}$F-mefway while the ethyl acetate fraction contains $^{18}$F-mefway and other lipophilic metabolites. Each of the ethyl acetate extracts were concentrated to a small volume (20 μL) and were spotted (along with standard, $^{18}$F-mefway) on a large TLC plate. The plate was eluted with $CH_2Cl_2$:$CH_3OH$, 9:1 in order to analyze for parent $^{18}$F-mefway and metabolites. The developed TLC plate was dried, apposed overnight to phosphor screen, and were read using the Phosphor Cyclone Imager (Packard Instruments Co., Boston Mass.). The amount of $^{18}$F-mefway was evaluated in digital light units (DLU/mm$^2$) using OptiQuant acquisition and analysis program (Packard Instruments Co.). All blood samples were counted for radioactivity in a Packard Gamma Counter 5000 series.

Uptake of $^{18}$F-mefway in various regions was rapid and in less than 2 mins reached levels greater than 0.03% injected dose/mL. This is comparable to levels attained by $^{18}$F-MPPF, $^{18}$F-6FPWAY and other related WAY-100635 derivatives in monkey PET studies. After 3 hrs, about 6% of the initial activity in the cerebellum was still present. A number of brain regions exhibited retention of $^{18}$F-mefway and was consistent with the presence of 5-HT1A receptors.

Figure 6:
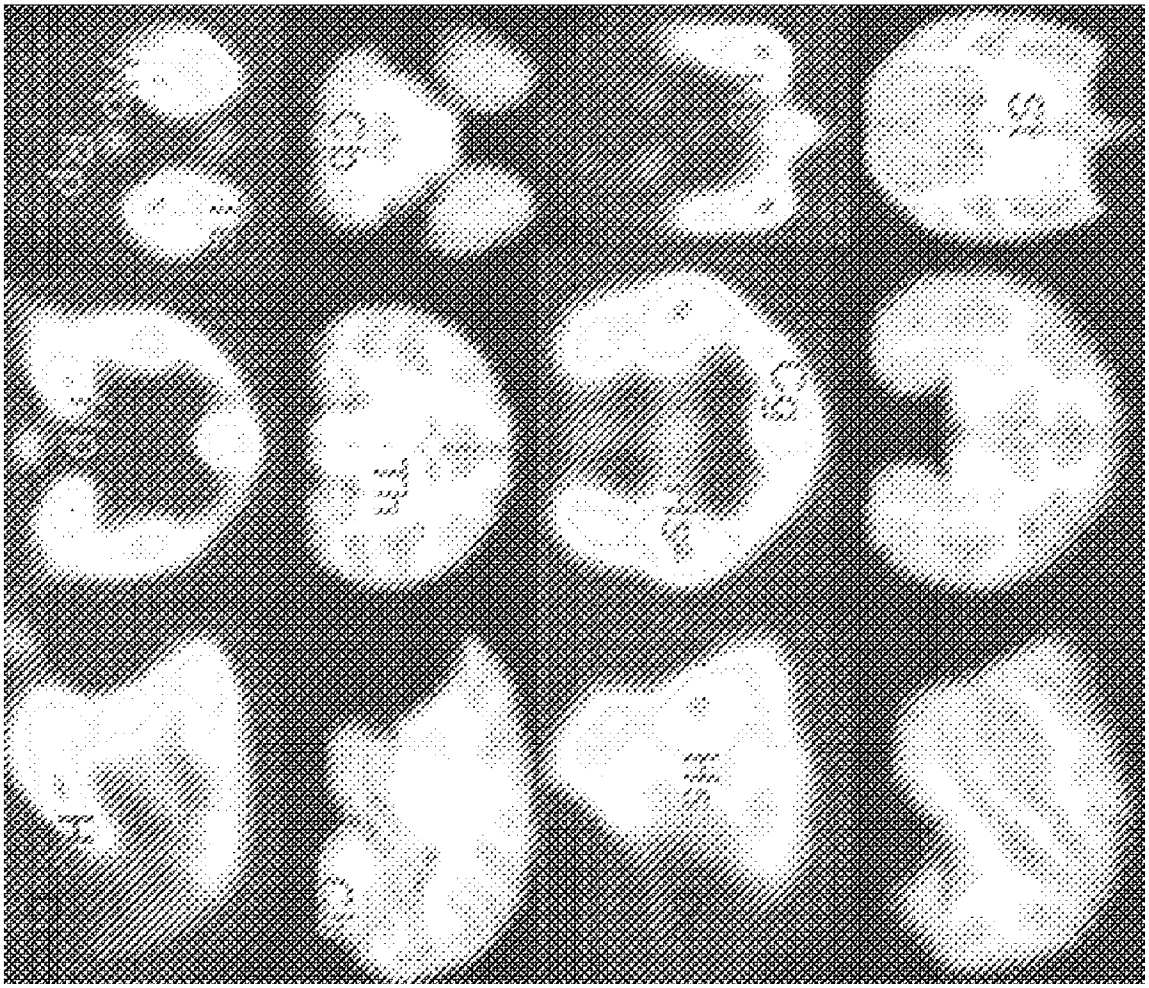
FIG. 6 depicts distribution of $^{18}$F-mefway in the rhesus monkey brain.

FIG. 6 depicts the distribution of $^{18}$F-mefway in the rhesus monkey brain. Coregistered MRI with summed PET images show localization of $^{18}$F-mefway. First and second rows are coregistered MR images and PET images, respectively, showing binding in various cortical regions, including distinct hot spot (Hs) seen in red near insular cortex. Third and fourth rows are coregistered MR images and PET images, respectively, showing hippocampus (seen in red in three slices) and raphe. Hs=hot spot; Cg=cingulate; Rp=raphe; St=striata; Oc=occipital cortex; Cb=cerebellum; Th=thalamus; Tc=temporal cortex.

It should be noted that time-activity curves for the various brain regions were taken and identified four sets of regions with different activity levels (data not shown). The highest binding regions relative to the cerebellum were the hippocampus and an area in the cortex, most probably associated with the insular cortex. Clearance from the cortical region was faster than that observed in the hippocampus. The second group comprised of temporal cortex, anterior cingulate/cingulate gyrus, frontal cortex and occipital cortex. The third group was the striatum, thalamus and raphe. Fourthly, the lowest binding region was the cerebellum. Cerebellum, containing little or no 5-$HT_{1A}$ receptors was taken as the reference region similar to the other 5-$HT_{1A}$ radiotracers. The highest ratio (between 8 to 10) was found for the hippocampus and the hot spot in the cortex. These ratios went down after plateauing around 80 mins, suggesting that a 90 to 120 min PET study should be sufficient to obtain quantitative information on receptor concentration. The second group of regions exhibited ratios between 5 and 8 was found for temporal cortex, frontal cortex, occipital cortex and anterior cingulate. All ratios decreased after peaking at approx. 80 mins. The third group of regions namely thalamus, striatum and raphe had ratios of 2-3.5. At the end of the 3 hr scan approx 60% of the initial activity in the hippocampus was still specifically bound and the hippocampus to cerebellum ratio had come down to 8.4 from a peak of 9.7.

Hydrophilic and lipophilic components were observed in the plasma during the PET study with $^{18}$F-mefway. Thee aqueous fraction is most likely comprised of the amide-hydrolysis product, $^{18}$F-4-fluoromethylcyclohexane carboxylic acid, analogous to other reported radiotracers such as $^{18}$F-FCWAY (Carson et al., 2003). Formation of this acid seems to plateau around 50-60% after 50 mins post-injection. Lipophilic components that were extracted into ethyl acetate indicated the presence of primarily the parent, $^{18}$F-mefway (FIG. 10), suggesting that radiolabeled $^{18}$F-mefway is the principal component in the brain. At 3 hours post injection, approximately 30% of $^{18}$F-mefway still remained unmetabolized in plasma. These levels are greater than those reported for some of the previous 5-$HT_{1A}$ radioligands.

Therefore, it should be appreciated that the radiotracer $^{18}$F-mefway provides excellent in vitro and in vivo binding characteristics to the 5-$HT_{1A}$ receptor. Most advantageously, the compound retains high binding affinity, displays optimal lipophilicity, and is radiolabeled efficiently with $^{18}$F-fluorine in a single step. Furthermore, the unexpected lack of any significant defluorination allowed for very high target to non-target ratios in receptor-rich regions both in vitro and in vivo. These improved ratios from currently used agents and therefore make $^{18}$F-mefway more suitable for human studies. Moreover, $^{18}$F-mefway's ability to be displaced by serotonin allows measuring serotonin concentration changes in the living brain.

Thus, specific embodiments and applications of compositions and methods related to serotonin 5-HT1A receptor ligands have been disclosed. It should be apparent, however, to those skilled in the art that many more modifications besides those already described are possible without departing from the inventive concepts herein. The inventive subject matter, therefore, is not to be restricted except in the spirit of the present disclosure. Moreover, in interpreting the specification and contemplated claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Furthermore, where a definition or use of a term in a reference, which is incorporated by reference herein is inconsistent or contrary to the definition of that term provided herein, the definition of that term provided herein applies and the definition of that term in the reference does not apply.

What is claimed is:

1. A compound having a structure according to Formula I

Formula I

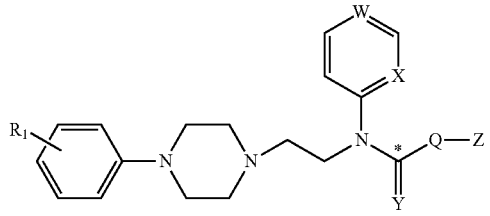

*or a pharmaceutically acceptable salt thereof;* wherein $R_1$ is [$OCH_3$ or $O^{11}CH_3$] *alkoxy*;

X is N, and W is CH;

Y is O, and wherein * denotes an optional $^{11}$C isotope;

Q is optionally substituted cycloalkyl [or cycloalkenyl]; and wherein Z is lower alkyl, *and wherein $^{18}$F is covalently bound to Z when $^{11}$C is absent in* *; and wherein $^{11}$C is present in at least one of $R_1$ and * *when $^{18}$F is absent and Z is $CH_2F$.*

2. The compound of claim 1 fun her comprising a pharmaceutically acceptable carrier in admixture with the compound to form a pharmaceutical composition, wherein the compound is optionally present as a salt with a pharmaceutically acceptable counter ion.

3. A method of *diagnosing or* treating a panic disorder, a bipolar disorder, or a seizure disorder, comprising a step of administering a pharmaceutical composition that includes a compound having a structure according to Formula I, *or a pharmaceutically acceptable salt thereof,* to a mammal, Formula I

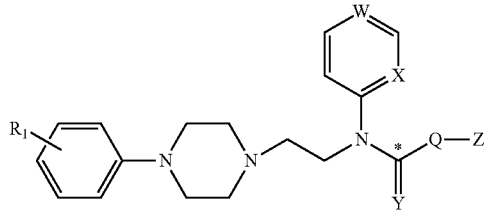

wherein $R_1$ is an optionally substituted lower alkyl, alkoxy, halogen, or hydrogen, and wherein at least one carbon atom in R1 may be $^{11}$C;

X and W are independently N or CH;

Y is O, $NR_1$, or S, and wherein * denotes an optional $^{11}$C isotope;

Q is optionally substituted cycloalkyl or cycloalkenyl; and wherein Z is lower alkyl, and wherein a PET detectable label is covalently bound to Z when $^{11}C$ is absent in $R_1$ and *, and wherein the PET detectable label is $^{11}C$ or $^{18}F$.

4. The method of claim 3 wherein [in the compound] Q is cyclohexyl or cyclohexenyl, and Z is $CH_2{}^{18}$ or $CH_2CH_2{}^{18}F$.

5. The method of claim 3 wherein [in the compound comprises $^{18}F$-Mefway] *the compound is*

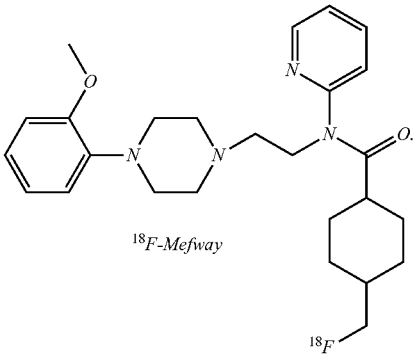

6. The method of claim 5 wherein [in the compound comprises] *the compound is* trans-$^{18}F$-Mefway

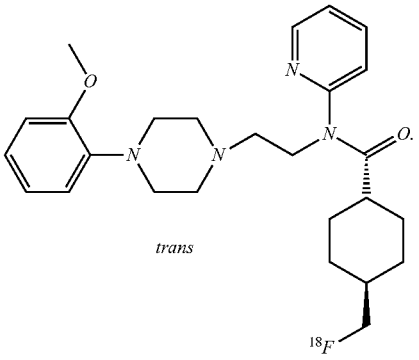

7. The method of claim 3 further comprising a step of performing at least one of a PET scan and a SPECT scan on the mammal.

8. The method of claim 3 wherein the pharmaceutical composition is parenterally administered.

9. The method of claim 3 wherein the composition comprises [$^{18}F$-Mefway]

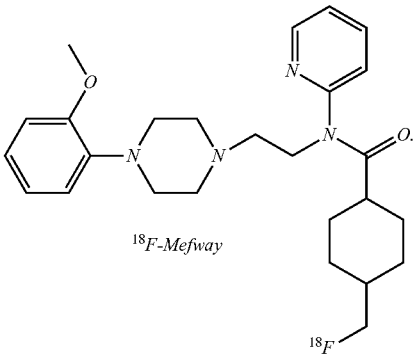

10. The method of claim 3 wherein the composition comprises trans-$^{18}F$-Mefway

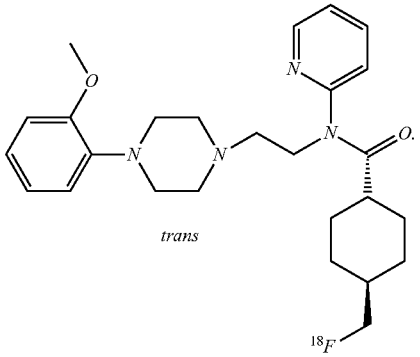

11. A method of quantifying serotonin in a neural tissue comprising:

a step of administering a pharmaceutical composition comprising a compound having a structure according to Formula I, *or a pharmaceutically acceptable salt thereof,* to a mammal, Formula I

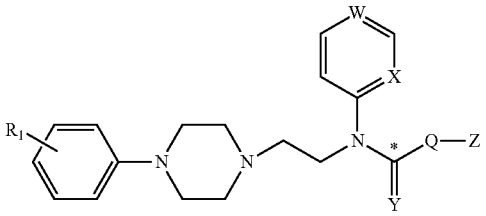

wherein $R_1$ is an optionally substituted lower alkyl, alkoxy, halogen, or hydrogen, and wherein at least one carbon atom in R1 may be $^{11}C$;

X and W are independently N or CH;

Y is O, $NR_1$, or S, and wherein * denotes an optional $^{11}C$ isotope;

Q is optionally substituted cycloalkyl or cycloalkenyl; and wherein Z is lower alkyl, and wherein a PET detectable label is covalently bound to Z when $^{11}C$ is absent in $R_1$ to *, and wherein the PET detectable label is $^{11}C$ or $^{18}F$, *and wherein Z is $CH_2F$ when $^{11}C$ is present in $R_1$ or *;* a step of performing a PET scan on the tissue, and a step of correlating a PET signal quantity with a serotonin concentration in the tissue.

12. The method of claim 11 wherein [in the compound] Q is cyclohexyl or cyclohexenyl, and Z is $CH_2{}^{18}F$ or $CH_2CH_2{}^{18}F$.

*13. A compound having a structure according to Formula II*

*Formula II*

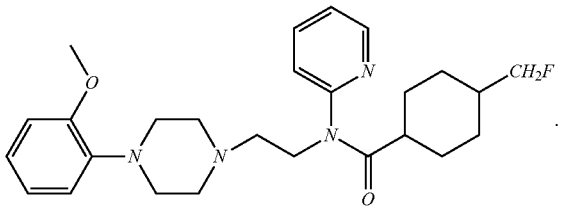

14. A compound having a structure according to Formula III

Formula III

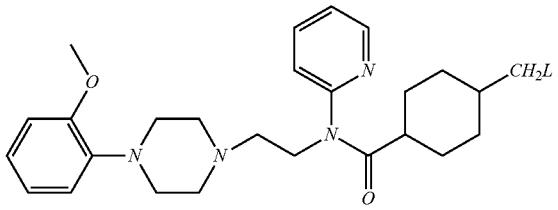

wherein L is a leaving group.

15. The compound of claim 14 wherein L is selected from the group consisting of halogen, O-mesylate, O-tosylate, O-nosylate, and O-brosylate.

16. A method for imaging the 5-HT1A receptor comprising:

(i) administering a pharmaceutical composition comprising a compound having a structure according to Formula I to a mammal

I

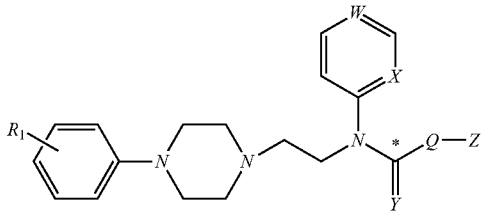

or a pharmaceutically acceptable salt thereof;

wherein $R_1$ is an optionally lower alkyl, alkoxy, halogen, or hydrogen, and wherein at least one carbon atom in $R_1$ is optionally $^{11}C$;

X and W are independently N or CH;

Y is O, $NR_1$, or S, and wherein * denotes an optional $^{11}C$ isotope;

Q is optionally substituted cycloalkyl or cycloalkenyl; and

Z is lower alkyl, and wherein a PET detectable label is covalently bound to Z when $^{11}C$ is absent in $R_1$ and *, and wherein the PET detectable label is $^{11}C$ or $^{18}F$, and wherein Z is $CH_2F$ when $^{11}C$ is present in $R_1$ or *; and (ii) performing a PET scan on said mammal.

17. A method of quantifying serotonin in vivo comprising:

(i) administering a pharmaceutical composition comprising a compound having a structure according to Formula I, or a pharmaceutically acceptable salt thereof, to a mammal

I

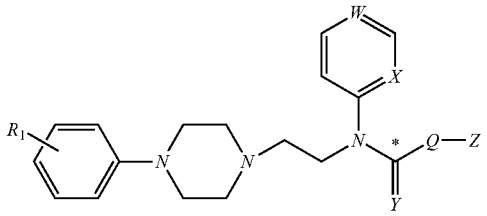

wherein $R_1$ is an optionally lower alkyl, alkoxy, halogen, or hydrogen, and wherein at least one carbon atom in R1 is optionally $^{11}C$;

X and W are independently N or CH;

Y is O, $NR_1$, or S, and wherein * denotes an optional $^{11}C$ isotope;

Q is optionally substituted cycloalkyl; and

Z is lower alkyl, and wherein a PET detectable label is covalently bound to Z when $^{11}C$ is absent in $R_1$ and *, and wherein the PET detectable label is $^{11}C$ or $^{18}F$, and wherein Z is $CH_2F$ when $^{11}C$ is present in $R_1$ or *;

(ii) performing a PET scan on said mammal; and (iii) correlating a PET signal quantity with a serotonin concentration.

18. A ligand-receptor complex comprising:

(i) a compound having a structure according to Formula I

I

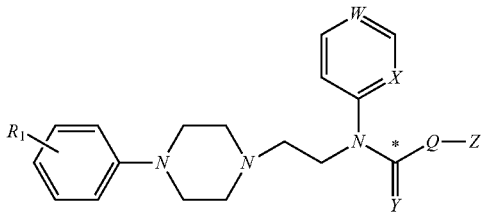

wherein $R_1$ is an optionally lower alkyl, alkoxy, halogen, or hydrogen, and wherein at least one carbon atom in $R_1$ is optionally $^{11}C$;

X and W are independently N or CH;

Y is O, $NR_1$, or S, and wherein * denotes an optional $^{11}C$ isotope;

Q is optionally substituted cycloalkyl; and

Z is lower alkyl, and wherein a PET detectable label is covalently bound to Z when $^{11}C$ is absent in $R_1$ and *, and wherein the PET detectable label is $^{11}C$ or $^{18}F$, and wherein Z is $CH_2F$ when $^{11}C$ is present in $R_1$ or *; and (ii) a 5-HT1A receptor.

* * * * *

UNITED STATES PATENT AND TRADEMARK OFFICE

CERTIFICATE OF CORRECTION

PATENT NO. : RE43,688 E
APPLICATION NO. : 13/187728
DATED : September 25, 2012
INVENTOR(S) : Jogeshwar Mukherjee, Neil Saigal and Harsh Saigal It is certified that error appears in the above-identified patent and that said Letters Patent is hereby corrected as shown below:

In the Claims:

In Col. 20, line 30
replace "...where in $R_1$ is [$OCH_3$ or $O^{11}CH_3$] alkoxy;"
with "...where in $R_1$ is alkoxy, [$OCH_3$ or $O^{11}CH_3$];

In Col. 20, line 39
replace "...claim 1 fun her comprising..."
with "...claim 1 further comprising..."

In Col. 21, line 6
replace "...and Z is $CH_2^{18}$ or $CH_2CH_2^{18}F$."
with "...and Z is $CH_2^{18}F$ or $CH_2CH_2^{18}F$."

Signed and Sealed this
Thirteenth Day of August, 2013

Teresa Stanek Rea
*Acting Director of the United States Patent and Trademark Office*